United States Patent
Kreizman et al.

(10) Patent No.: US 6,258,104 B1
(45) Date of Patent: Jul. 10, 2001

(54) METHOD AND APPARATUS FOR REMOVING TISSUE FROM A REGION OF INTEREST USING STEREOTACTIC RADIOGRAPHIC GUIDANCE

(75) Inventors: Alexander S. Kreizman, Beechurst; Kenneth F. Defrietas, Patterson, both of NY (US); Alan W. Rego, Woodbury, CT (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 09/641,998

(22) Filed: Aug. 18, 2000

Related U.S. Application Data

(62) Division of application No. 09/183,682, filed on Oct. 30, 1998, now Pat. No. 6,182,573.

(51) Int. Cl.[7] ....................................... A61B 6/00
(52) U.S. Cl. ............................................. 606/130
(58) Field of Search .................... 600/429, 431, 600/439; 606/130

(56) References Cited

U.S. PATENT DOCUMENTS

| | | |
|---|---|---|
| 4,727,565 | 2/1988 | Ericson . |
| 5,289,520 | 2/1994 | Pellegrino et al. . |
| 5,373,844 * | 12/1994 | Smith et al. ................. 128/653.1 |
| 5,594,769 | 1/1997 | Pellegrino et al. . |
| 5,609,152 | 3/1997 | Pellegrino et al. . |
| 5,735,264 | 4/1998 | Siczek et al. . |
| 5,830,219 | 11/1998 | Bird et al. . |

OTHER PUBLICATIONS

"Stereotactic Mammography Imaging System With Prone Position Exmaination Table and CCD Camera", Pellegrino et al., Abstract of Patent No. 5,289,520 issued Feb. 22, 1994.

Ultrasonic Mucosal Proctectomy Without Endorectal Pull–through by T. Heimann, R. Kurtz, S. Shen–Schwartz, A. Aufses, Jr., from *Diseases of the Colon and Rectum*, May 1985, vol. 28, No.5.

Techniques of Ultrasonic Dissection in Resection of the Liver by C. Putnam, reprint from *Surgery Gynecology & Obstetrics*, Nov. 1983, vol. 157, 474–78.

A Bloodless Technique for Tongue Surgery by J. Weitz, W. Hodgson, L. Loscalzo, A. McElhinney, *Head & Neck Surgery*, Jan./Feb. 1981, pp. 244–46.

Cavitrons in Urologic Surgery by J. Addonizio and M. Choudhury, "Lasers and Other Technologic Advances in Urology," *Urologic Clinics of North America*, vol. 13, No. 3, Aug. 1986, pp. 445–454.

Use of the Cavitron Ultrasonic Surgical Aspirator and Evoked Potentials for the Treatment of Thalamic and Brain Stem Tumors in Children, A. Albright, R. Sclabassi, *Neurosurgery*, vol. 17, No. 4, 1985, pp. 564–568.

(List continued on next page.)

*Primary Examiner*—William E. Kamm
(74) *Attorney, Agent, or Firm*—Ware, Fressola, Van Der Sluys & Adolphson LLP

(57) ABSTRACT

A method and apparatus for removing tissue from a volume surrounding a region of interest with a body part of a patient is disclosed. The tissue removal volume and location is determined by stereotactic radiography. The size of the tissue removal volume surrounding the region of interest is derived by placing boundaries around the region of interest in each stereotactic radiographic image. A tissue removal tool is moved within the derived tissue removal volume. The tissue in the region of interest which has been previously diagnosed as cancerous can be marked with a radioactive isotope, for example, and the removal of such tissue from the removal volume which surrounds the region of interest can be monitored to determine whether the tissue in the region of interest has been completely removed.

6 Claims, 7 Drawing Sheets

OTHER PUBLICATIONS

Resection of Advanced Stage Neuroblastoma With The Cavitron Ultrasonic Surgical Aspirator by R. Loo, H. Applebaum, J. Takasugi, R. Hurwitz, *Journal of Pediatric Surgery*, vol. 23, No. 12, Dec. 1988, pp. 1135–438.

The CUSA® CEM™ System: A New Dimension of Efficiency by E. Laws, Jr., *Neurosurgery*, vol. 28, No. 3, Mar. 1991, published by Valleylab®/Pfizer.

Debulking Surgery for Ovarian Cancer with the Cavitron Ultrasonic Surgical Aspirator (CUSA)—A Preliminary Report by G. Deppe, V. Malviya, J. Malone, *Gynecologic Oncology* 31, 1988, pp. 223–226.

CUSA® System 200 Brochure published by Valleylab®1998.

* cited by examiner

METHOD AND APPARATUS FOR REMOVING TISSUE FROM A REGION OF INTEREST USING STEREOTACTIC RADIOGRAPHIC GUIDANCE

This application is a division of application Ser. No. 09/183,682, filed Oct. 30, 1998, now U.S. Pat. No. 6,182,573.

BACKGROUND OF THE INVENTION

1. Field of the Invention

The present invention generally relates to a method and apparatus for the removal of tissue from a region of interest in a body part of a patient. More particularly, the present invention relates to a method and apparatus for the removal of tissue from a region of interest in a body part of a patient, such as a breast, wherein the tissue removal is guided by stereotactic radiography.

2. Description of the Prior Art

Stereotactic niammographic devices have been used to determine the three dimensional coordinates of a region of interest in a breast relative to a point of reference on the stereotactic devices. The three dimensional coordinates are generally used for diagnostic and surgical procedures, and more particularly to insert the end of a wire, the tip of a biopsy needle or the tip of a rotary cutting tool into the region of interest in the breast. Wires are generally used to guide a surgeon to the region of interest to remove part or all thereof. The biopsy needle is typically used to sample cells or tissue from the region of interest. The rotary cutting tool is generally used for the removal of tissue from the region of interest.

One example of a stereotactic mammographic device is described in U.S. Pat. No. 5,289,520, which is incorporated by reference in its entirety. The commercial embodiment of the device described and illustrated in the patent has been used to guide a biopsy needle into a region of interest to obtain samples of cells and tissue. Also, such device has been used to guide rotary surgical cutting instruments to remove tissue from a region of interest.

As described in C. W. Putnam, "Techniques of Ultrasonic Dissection in Resection of the Liver", *Surgery, Gynecology & Obstetrics*, Vol. 157, pgs. 474–478, November, 1983, ultrasonic aspirated dissectors, such as the Cavitron Ultrasonic Surgical Aspirator, comprise a handpiece which is connected to a control console. The handpiece contains a water-cooled magnetostrictive transducer that activates a hollow titanium tip along its longitudinal axis at a frequency of approximately 23,000 cycles per second. The tip of the handpiece is irrigated and a suction line is connected to the hollow tip to aspirate the irrigant, blood and tissue fragments. The instrument works by generating ultrasonic vibrations which selectively fracture tissue in proportion to its water content. The fractured tissue is removed via the suction line.

Typically such ultrasonic surgical aspirators are controlled by hand in an open surgical procedure which is not minimally invasive. However, as the above referenced article suggests, such devices are used because they afford greater differentiation between the various types of tissue structure found during a surgical procedure involving a liver, for example. Heretofore, it is not believed that an ultrasonic surgical aspirator has generally been used as a minimally invasive tool to remove tissue from a region of interest in a patient's body part, such as a breast, nor has such a tool been guided by a stereotactic radiographic device to remove tissue from the region of interest.

SUMMARY OF THE INVENTION

Accordingly, it is a principal object of the present invention to guide an ultrasonic surgical aspirating tissue removal tool to a region of interest inside a patient's body part.

It is another object of the present invention to guide and control a tissue removal tool within a volume surrounding a region of interest inside a patient's body part.

These objects are accomplished, at least in part, by providing a method and apparatus for removing tissue from a volume surrounding a region of interest within the body part of a patient. The apparatus comprises a body part holder adapted to hold the body part immobile. It also defines a predetermined point of reference relative to the immobile body part. The apparatus employs a stereotactic imaging assembly having an radiation transmission source adapted to receive operating instruction signals and to irradiate the body part, and a radiation receiver adapted to transmit image signals corresponding to radiation received from the transmission source passing through the body part to obtain stereotactic images of the held body part and the region of interest therein. The apparatus includes a display adapted to receive display signals and to display stereotactic images of the body part and region of interest therein corresponding to the display signals received. A user interface, adapted to interactively enable a user to place a boundary around the region of interest of the body part displayed, provides boundary signals representing the dimensions and location thereof around the region of interest. The apparatus also includes a motorized tissue removal tool guiding stage capable of moving relative to the predetermined point of reference. The removal tool guiding stage is adapted to receive drive signals to drive the stage to a position relative to the predetermined point of reference and is further adapted to provide position indicating signals to indicate the position of the stage relative to the predetermined point of reference. A tissue removal tool is held by the tool guiding stage. The tissue removal tool has a fragmenting tip and a means for extracting or removing fragmented tissue from the fragmenting tip. The apparatus is directed by a controller adapted to: provide operating signals to the radiation source to cause the radiation source to transmit radiation; receive image signals from the radiation receiver; provide display signals to the display based upon the image signals received; receive boundary signals from the user interface; provide boundary display signals to the display based upon the boundary signals received; calculate the size and location of a tissue removal volume relative to the predetermined point of reference based upon the boundary signals received; provide drive signals to the motorized guiding stage to command the stage to move to a position within the calculated tissue removal volume; and receive position indicating signals from the guiding stage.

The method of the present invention comprises several steps including: holding a body part of a patient having a region of interest therein relative to a predetermined point of reference; obtaining stereotactic images of the body part containing the region of interest therein; and displaying the stereotactic images. Once the stereotactic images are displayed, the method involves the following additional steps: placing a boundary around the region of interest in each displayed stereotactic image; determining the size and location of a tissue removal volume surrounding the region of interest relative to the predetermined point of reference from the location, dimensions and relative geometry of the boundaries; holding a tip of a tissue removal tool relative to the predetermined point of reference; and moving the tip of the tissue removal tool within the tissue removal volume to remove tissue from within the tissue removal volume.

Other objects and advantages of the present invention will become apparent to those skilled in the art from the following detailed description read in conjunction with the attached drawings and claims appended hereto.

BRIEF DESCRIPTION OF THE DRAWINGS

The drawings, not drawn to scale, include.

DETAILED DESCRIPTION OF THE INVENTION

The present invention relates to a method and apparatus for removing tissue from a volume surrounding a region of interest in a body part. While the present invention will be discussed in the context of a suspicious lesion contained within a breast which has been previously diagnosed by mammographic biopsy procedures, those skilled in the art will appreciate that the present invention may be used on other body parts containing regions of interest in which tissue is to be removed. The apparatus of the present invention will be discussed first followed by a discussion of the method.

The Apparatus

Figure 1:
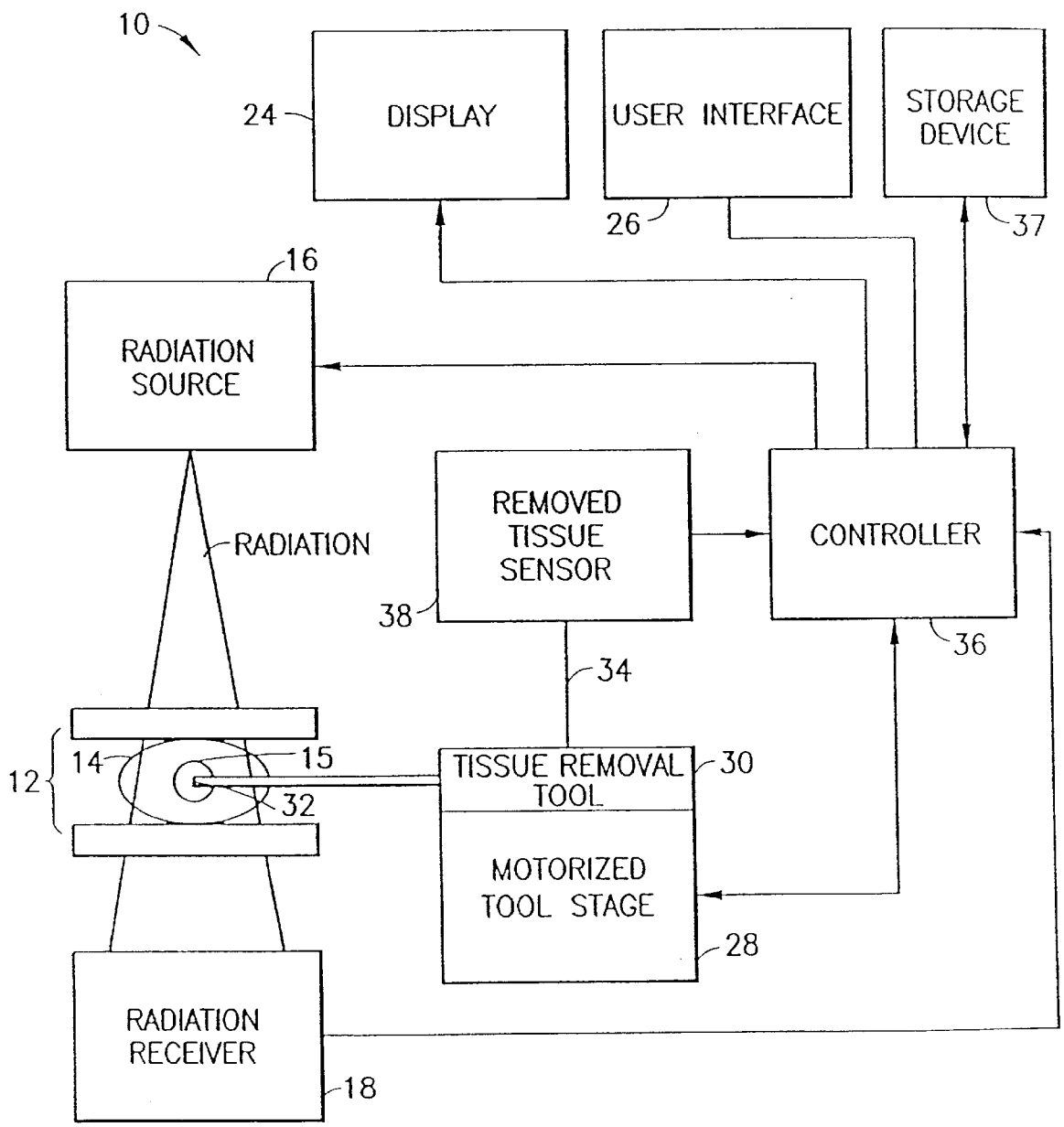
FIG. 1 is a schematic diagram of the apparatus for removing tissue and for monitoring the tissue removal method

Referring to FIG. 1, the apparatus for removing tissue from a volume surrounding a region of interest within the body part of a patient is comprised of several components. The apparatus 10 includes a body part holder 12 adapted to hold a body part 14, such as a breast, immobile and to define a predetermined point of reference. It also includes a stereotactic imaging assembly having a radiation transmission source 16 adapted to receive operating instruction signals and to irradiate the body part 14, and a radiation receiver 18 adapted to transmit image signals corresponding to radiation received from the transmission source 16 passing through the body part 14. The imaging assembly is further adapted to obtain stereotactic images of the body part 14 held by holder 12 and the region of interest therein.

The apparatus also includes a display 24 which adapted to receive display signals and to display stereotactic images of the body part 14 and region of interest therein corresponding to the display signals received. The display 24 may be an ordinary video display having suitable contrast and spatial resolution capacity to permit visualization of the region of interest within the body part.

The apparatus is further provided with a user interface 26 that is adapted to enable a user to interactively provide a visible boundary around the region of interest in the body part 14 displayed in each stereotactic image. Such an interface may be a keyboard, mouse, joystick or trackball, for example, which interfaces with controlling software. The interface also enables a boundary signal representing the dimensions and position of the visible boundary to be formed for each boundary which is used for calculating a tissue removal volume as described below.

The apparatus further includes a motorized tissue removal tool guiding stage 28 capable of moving relative to the predetermined point of reference defined by the holder 12. The removal tool is adapted to receive drive signals to drive the stage 28 to one or more positions relative to the predetermined point of reference. The stage is also adapted to provide position indicating signals to indicate the position of the stage relative to the predetermined point of reference defined by the holder 12.

A tissue removal tool 30 is held by the tool guiding stage 28. Preferably, the tissue removal tool has a fragmenting tip 32 and a conduit 34 for extracting or removing fragmented tissue from the fragmenting tip 32.

The above described components of the apparatus are controlled by a controller 36, which may be formed by any commercially available computer having sufficient processing speed and memory such as a computer having a Intel Pentium II™ processor operating at 300 Mhz with 64 MBytes of RAM. The controller 36 is adapted to coordinate a number of functions of the apparatus including: providing operating signals to the radiation source 16 to cause the radiation source to transmit radiation; receiving image signals from the radiation receiver 18; providing display signals to the display 24 based upon the image signals received; receiving boundary signals as created by the user interface 26; providing boundary display signals to the display 24 based upon the boundary signals received; calculating the size and location of a tissue removal volume relative to the predetermined point of reference defined by the holder 12 based upon the boundary signals received. The controller also provides drive signals to the motorized guidingy stage 28 to command the stage to move to a position within the calculated tissue removal volume, and receives position indicating signals from the guiding stage 28.

A more advanced embodiment of the present invention includes a removed tissue sensor 38 connected to the tissue removal tool's conduit 34. Extracted tissue is passed through the tissue sensor via the conduit 34. The tissue sensor 38 is adapted to sense whether removed tissue contains a detectable marking substance which has been injected into the body part with the intention of marking the tissue in the region of interest with the detectable marking substance. The removed tissue sensor is further adapted to provide sensing signals to the controller 36 and it in turn is suitably adapted to receive such signals from the tissue sensor. It is known to use certain radioactive isotopes to mark cancerous tissue because such isotopes tend to concentrate around such tissue. Thus, assuming that the region of interest is comprised of cancerous tissue, the tissue removed from the region of interest should cause the sensor 38 to indicate that the tissue was in the region of interest due to the high concentration of radioactive isotopes being, present in the removed tissue. Assuming that the tissue surrounding the region of interest is not cancerous and therefore there is no concentration or a low concentration of radioactive isotopes, the material removed around the region of interest, but outside thereof, will typically not be sensed by the tissue sensor 38 if the threshold for the sensor is correctly calibrated.

The apparatus may be provided with an optical or magnetic data storage device 37 that can store the signals generated by the tissue sensor and the position indicating signals from the stage 28. The data may be recalled from the storage device 37 by the controller to form and display a map of the tissue sensor signal versus the position indicating signal.

Figure 2:
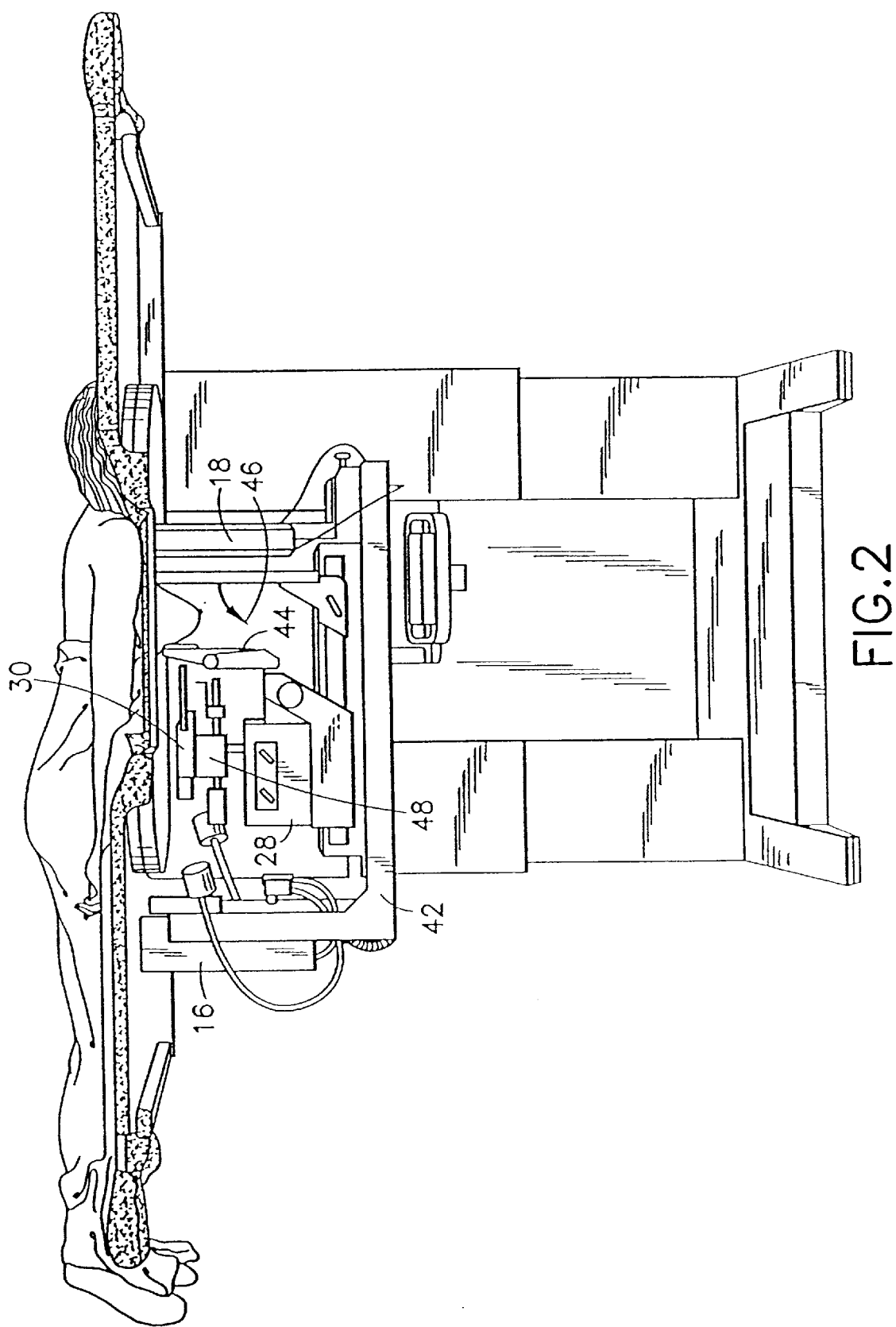
FIG. 2 is a side view of a stereotactic mammography needle biopsy apparatus for guiding and controlling an ultrasonic surgical aspirating tissue removal tool according to the method of the present invention.

FIG. 2 illustrates a prone stereotactic mammography apparatus which is typically used for stereotactic mammographic guided needle biopsies of the breast and which may be used with the present invention. A detailed description of the prone stereotactic apparatus 10 can be found in U.S. Pat. No. 5,289,520, which is incorporated herein by reference. The StereoGuide™ stereotactic mammography apparatus which is commercially available from Trex Medical Corporation is a device operating under the configurations and principals described in U.S. Pat. No. 5,289,520.

Generally, the stereotactic apparatus depicted in FIG. 1 has a stereotactic imaging assembly comprising an X-ray tube 16 and an image receiver 18 mounted on an imaging arm 42 capable of moving relative to the breast to provide two stereotactic images. The apparatus has a holder 12 for holding the breast immobile and compressed. More specifically, the holder 12 comprises a movable compression paddle 44 and movable compression plate 46 and these define a predetermined point of reference about the breast 14.

The configuration of the stereotactic apparatus illustrated in FIG. 1 is preferred in the present invention due to image acquisition advantages resulting from the relative configuration of the imaging arm and compression arm. Such advantageous configuration is described in U.S. Pat. No. 5,289,250 and U.S. Pat. No. 5,594,769, which is incorporated herein by reference. However, other stereotactic mammography biopsy devices, including both upright and prone using other imaging and compression configurations may also be used. An example of such other configurations may be found in Ericson, U.S. Pat. No. 4,727,565, entitled "Method of Localization."

The stereotactic apparatus 10 illustrated in FIG. 1 contains a motorized guiding stage 28 which may be adapted for the purposes of the present invention. Typically the stage is used for guiding a biopsy needle instrument or rotary cutting tool, held in holder 48 that is suitably adapted for holding such devices. According to the present invention, the holder 48 may be modified, as required, to hold an ultrasonic surgical aspiration tissue removal tool in a manner in which the tip of such tool may be guided to a region of interest within a breast pendulantly presented in the stereotactic apparatus, as illustrated. In the case of the ultrasonic aspirated tool depicted in FIG. 3, as further discussed below, the holder needs to be fabricated so that it will not interfere with the tool's operation.

Figure 3:
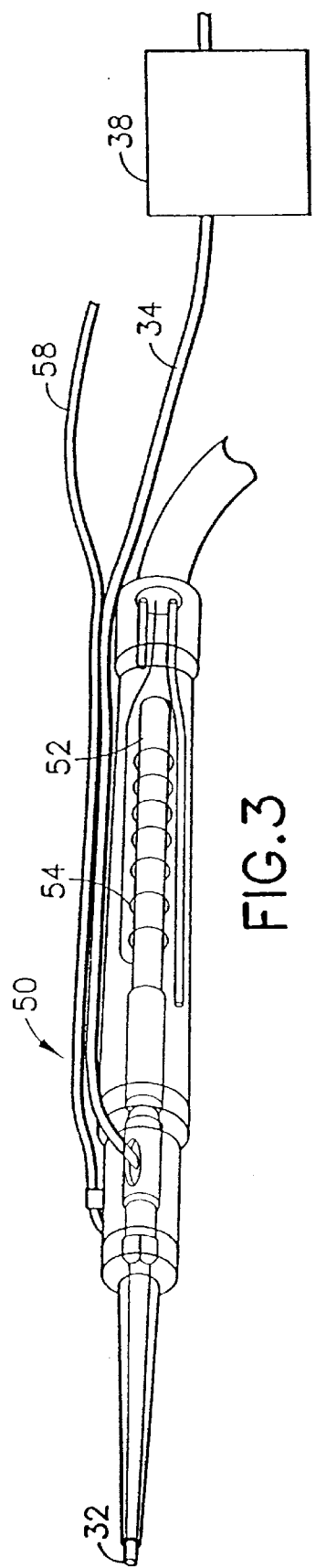
FIG. 3 is a perspective view of an ultrasonic aspiration device.

FIG. 3 illustrates a commercially available ultrasonic aspirated tissue removal tool 50 made by Valleylab, Inc., and marketed under the trademark CUSA™. The tool comprises a transducer 52 surrounded by an electric coil 54. The coil causes the transducer, and the tip 32 thereof, to vibrate at ultrasonic frequencies. The tool also includes an irrigation duct 58 for providing irrigation at the tip 32 and the aspiration conduit 34 which provides an aspiration source to remove tissue fragments located at or near the tip 32. As described above, the conduit 34 may be connected to the tissue sensor 38. Removed tissue in the conduit 34 may be passed through the sensor to determine whether the tissue removed is from the region of interest as such tissue contains a marking substance that can be detected by the sensor. While the CUSA™ ultrasonic aspirated tissue removal tool has been discussed herein, those skilled in the art will appreciate that other configurations of ultrasonic aspirated tissue removal tools will also work for the purposes of the present invention. Also, those skilled in the art will also appreciate that other types of tissue removal tools may also be employed in the present invention.

Figure 4A:
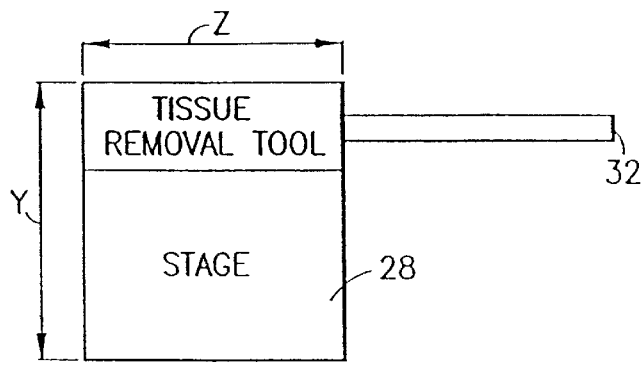
FIGS. 4A, 4B and 4C are side, front and overhead schematic views of the aspirator and stage.
Figure 4B:
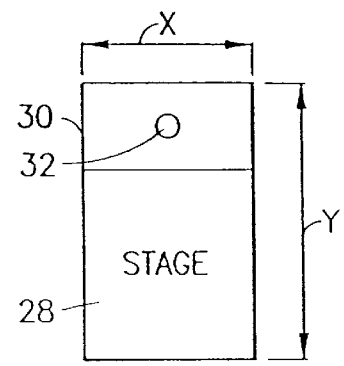
Figure 4C:
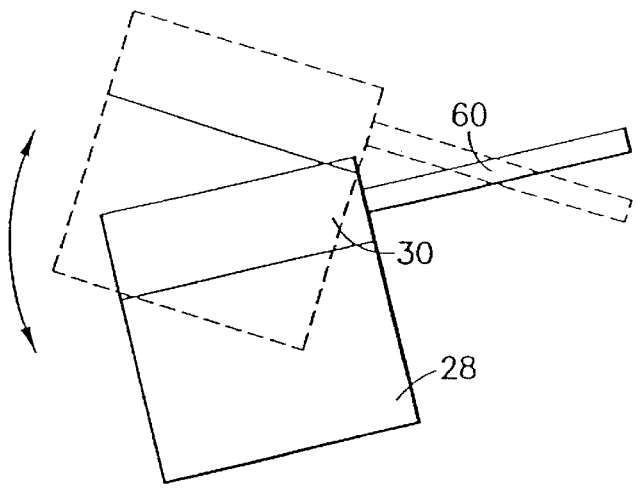
Figure 5A:
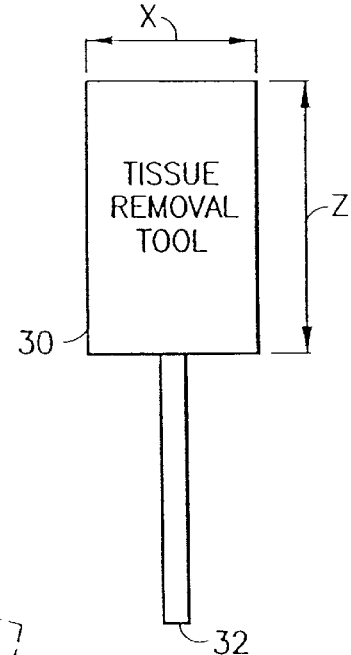
FIGS. 5A and 5B are schematic illustrations of the aspirator and stage pivoting about a pivot point.
Figure 5B:
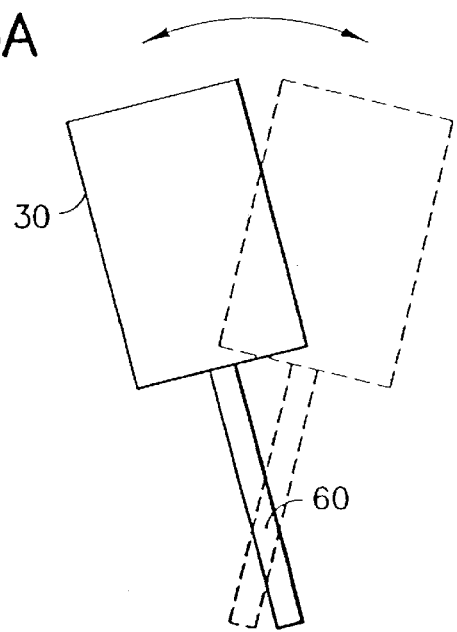

FIGS. 4A, 4B and 4C are side, front and overhead schematic views of the aspirator and stage illustrating the X, Y and Z directions of the orthogonal movement of the stage 28 and ultrasonic aspirated tissue removal tool 30. FIGS. 5A and 5B illustrate that the stage 28 may be further pivoted, if desired, about an arbitrarily selected pivot point 60 of the aspirator.

The Method

The method for removing tissue from a volume surrounding a region of interest within the body part of a patient comprises several steps which will be described further below with general reference to FIG. 6. In the method 100, the first step (step 102) is to hold a body part of a patient having a region of interest therein. Such holding also establishes a predetermined point of reference for the apparatus.

The next step (step 104) in the method is to obtain stereotactic images of the body part 14 containing the region of interest 15 therein. This step is performed in an ordinary manner, for example, as described in U.S. Pat. No. 5,289,520. Once the images are obtained, they are displayed (step 106) as illustrated in FIGS. 7A and 7B together with the point of reference 17.

Figure 6:
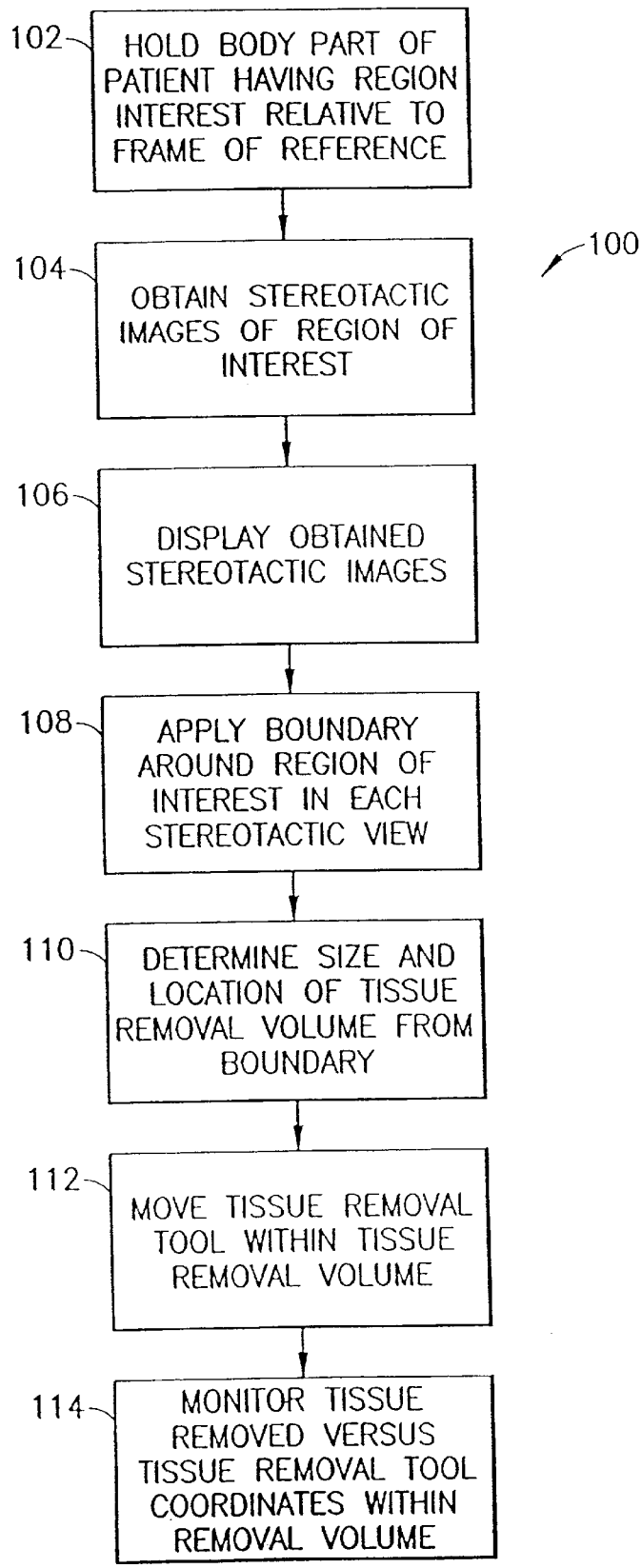
FIG. 6 is a flow diagram of the method of the present invention.
Figure 7A:
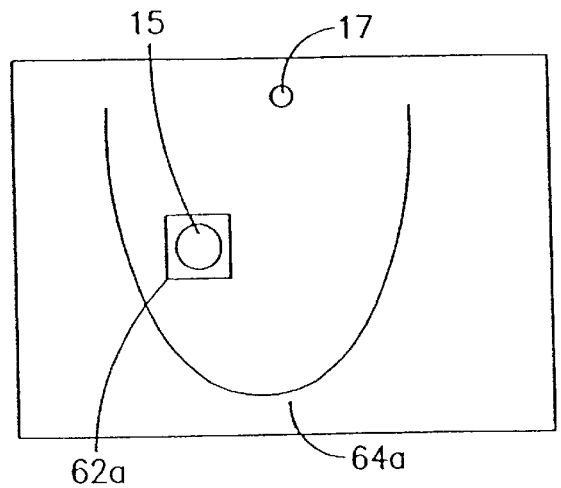
FIGS. 7A and 7B are plan views of left and right stereotactic images of a breast containing a region of interest.
Figure 7B:
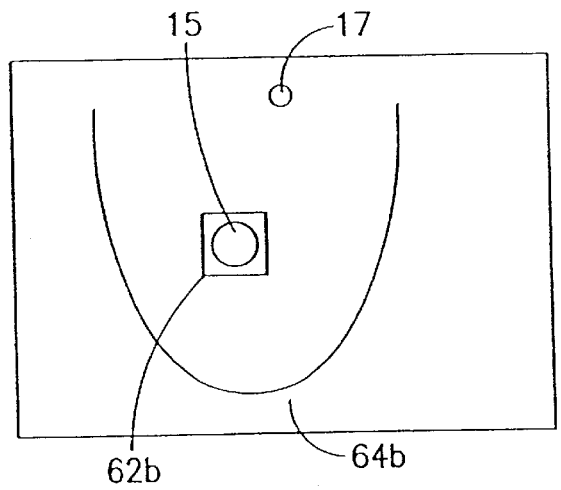
Figure 8:
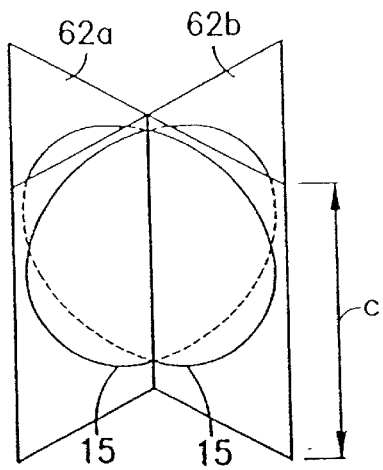
FIG. 8 is a combined perspective view of the geometrical relationship of the boundaries drawn around the region of interest displayed in the stereotactic images.
Figure 9:
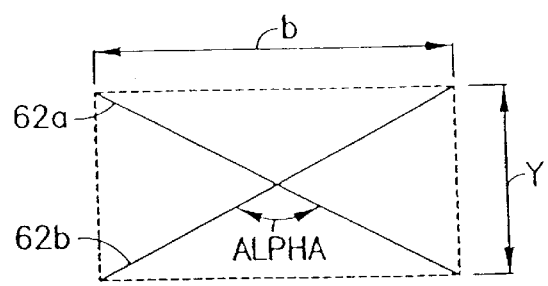
FIG. 9 is a plan view of the geometrical relationship of the boundaries drawn around the region of interest further illustrating the derivation of the tissue removal volume.

As further illustrated in FIGS. 6, 7A and 7B, via the user interface, a boundary 62a, 62b is interactively placed (step 108) around the region of interest 15 appearing in each displayed stereotactic image 64a, 64b. Referring to FIGS. 6, 8 and 9, the controller 20 calculates the size and three dimensional location of a tissue removal volume 66 surrounding the region of interest 15 relative to the predetermined point of reference based upon the location, relative geometry and dimensions of the boundaries 62a, 62b. The three dimensional location of the removal volume is calculated in an ordinary manner for calculating the position of a region of interest appearing in stereotactic images relative to the point of reference 17 appearing in the images. A description of such calculations is provided in U.S. Pat. No. 5,289,520.

The dimensions of the removal volume 66 are defined by the letters a, b, c in FIGS. 8 and 9. As illustrated in FIG. 9, the dimensions a and b are derived by drawing a rectangular perimeter around the crossing diagonals formed by the boundaries 62a, 62b when the perspective view of FIG. 8 is viewed overhead as :in FIG. 9. Dimensions a and b will vary according to the dimensions of the boundaries 62a, 62b drawn around the region of interest and the angle (alpha) used for stereotactic imaging. Dimension c is the height of the boundaries, which will vary according to the dimensions of the boundaries drawn around the region of interest. The method preferably assumes that the dimensions of the boundaries 62a, 62b placed over the regions of interest in the respective stereotactic images 64a, 64b are the same. This will have the affect of simplifying and speeding the calculations. However, the assumption is not absolutely required for the purpose of the present invention. Also, the boundaries 62a, 62b have been illustrated as being square. However, those skilled in the art will now appreciate that the boundaries 62a, 62b need not be square in shape, they could be rectangular, circular or elliptical, for example, and the shape of the calculated removal volume 66 will change accordingly since its dimensions and shape are dictated by the dimensions and shape of the boundaries 62a, 62b.

As further illustrated in FIG. 6, the next step (step 110) is holding a tip of a tissue removal tool relative to the predetermined point of reference and such step is followed by moving the tip of the tissue removal tool (step 112) within the tissue removal volume 66 to remove tissue from within the tissue removal volume. If desired, the tissue in the region of interest 15 may be marked with a radioactive isotope and the removal of such tissue may be monitored (step 114) to develop a three dimensional map of the tissue removal process versus coordinates of the tissue removal tool's tip, which is derived from knowledge of the position of the tip relative to the guiding stage and guiding stage position.

Figure 10:
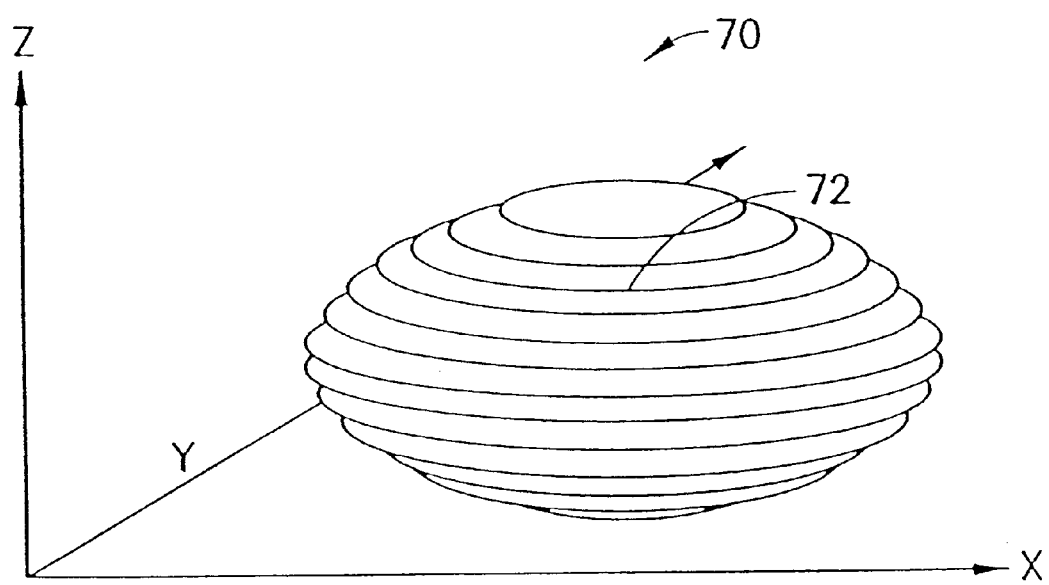
FIG. 10 is a three dimensional plot of the sensor indications versus the removal tool position in terms of Cartesian coordinates.

An exemplary map 70 from such step is illustrated in FIG. 10. A three dimensional pattern 72 versus the orthogonal coordinates of the tip of the tissue removing tool is depicted. The pattern is comprised of a plurality of points indicating that the tissue sensor detected marked tissue or did not detect marked tissue. The pattern provides an image of the results from the tissue removal surgical procedure.

It will thus be seen that the objects and advantages set forth above and those made apparent from the preceding descriptions, are efficiently attained and, since certain changes may be made in the above construction without departing from the scope of the invention, it is intended that the matter contained in the above description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A method for removing tissue from a volume surrounding a region of interest within the body part of a patient, the method comprising the steps of:

holding a body part of a patient having a region of interest therein relative to a predetermined point of reference;

obtaining stereotactic images of the body part containing the region of interest therein;

displaying the stereotactic images;

placing a boundary around the region of interest in each displayed stereotactic image;

determining the dimensions and location of a tissue removal volume surrounding the region of interest relative to the predetermined point of reference from the location, dimensions and relative geometry of the boundaries;

holding a tip of a tissue removal tool relative to the predetermined point of reference; and moving the tip of the tissue removal tool within the tissue removal volume to remove tissue from within the tissue removal volume.

2. The method of claim 1, further comprising the steps of:

injecting a substance within the body part to mark the tissue in the region of interest; and sensing the tissue removed by the tissue removal tool to determine whether tissue being removed from the tissue removal volume is marked tissue from the region of interest.

3. The method of claim 2, further comprising the step of:

recording the sensing of marked tissue versus the position of the tissue removal tool tip within the tissue removal volume.

4. The method of claim 3, further comprising the step of displaying the recording.

5. The method of claim 4, wherein the displaying is performed when the tip of the tissue removal tool has moved completely within the tissue removal volume.

6. An apparatus for removing tissue from a volume surrounding a region of interest within the body part of a patient, the apparatus comprising:

means for holding a body part of a patient having a region of interest therein relative to a predetermined point of reference;

means for obtaining stereotactic images of the region of interest within the body part;

means for displaying the stereotactic images;

means for placing a boundary around the region of interest in each of the displayed stereotactic image;

means for determining the size and location of a tissue removal volume surrounding the region of interest relative to the predetermined point of reference from the boundaries;

a tissue removal tool having a tip;

means for holding the tip of the tissue removal tool relative to the predetermined point of reference; and means for moving the tip of the tissue removal tool relative to the tissue removal tool and within the previously determined tissue removal volume to remove tissue from within the tissue removal volume.

* * * * *

UNITED STATES PATENT AND TRADEMARK OFFICE
CERTIFICATE OF CORRECTION

PATENT NO. : 6,258,104 B1
DATED : July 10, 2001
INVENTOR(S) : Kreizman et al.

Page 1 of 1

It is certified that error appears in the above-identified patent and that said Letters Patent is hereby corrected as shown below:

<u>Title page,</u>
Item [75], Inventors, delete "Kenneth F. Defrietas" and insert -- Kenneth F. DeFreitas --.
Item [62], Related U.S. Application Data, delete "09/183,682, filed on Oct. 30, 1998, now Pat. No. 6,182,573 " and insert -- 09/185,682, filed on Nov. 4, 1998, now Pat. No. 6,214,018 --.

Signed and Sealed this

Twenty-ninth Day of January, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.    : 6,258,104 B1
DATED         : July 10, 2001
INVENTOR(S)   : Kreizman et al.

It is certified that error appears in the above-identified patent and that said Letters Patent is hereby corrected as shown below:

Column 1,
Lines 6-7, delete "09/183,682, filed Oct. 30, 1998, now U.S. Pat. No. 6,182,573" and insert -- 09/185,682, filed Nov. 4, 1998, now U.S. Pat. No. 6,214,018 --.
Line 19, delete "niammographic" and insert -- mammographic --.

Column 4,
Line 49, delete "guidingy" and insert -- guiding --.

Column 5,
Line 3, delete "being, present" and insert -- being present --.

Column 6,
Line 22, delete "SA" and insert -- 5A --.
Line 63, delete ":in FIG. 9" and insert -- in FIG. 9 --.

Signed and Sealed this

Twenty-fifth Day of June, 2002

Attest:

JAMES E. ROGAN
Attesting Officer        Director of the United States Patent and Trademark Office